United States Patent [19]
Capel

[11] Patent Number: 6,125,301
[45] Date of Patent: Sep. 26, 2000

[54] USE OF TCET IN THE PROPHYLAXIS AND TREATMENT OF ALLERGIES

[75] Inventor: Ifor Donald Capel, Chaldon, United Kingdom

[73] Assignee: SPES Patents Limited, Bucks, United Kingdom

[21] Appl. No.: 09/202,609

[22] PCT Filed: Jun. 13, 1997

[86] PCT No.: PCT/GB97/01599

§ 371 Date: May 21, 1999

§ 102(e) Date: May 21, 1999

[87] PCT Pub. No.: WO97/48445

PCT Pub. Date: Dec. 24, 1997

[30] Foreign Application Priority Data

Jun. 17, 1996 [GB] United Kingdom .................. 9612628

[51] Int. Cl.$^7$ .................................................. A61N 1/32
[52] U.S. Cl. ............................................................ 607/74
[58] Field of Search ................................ 607/2, 72–74, 607/139, 140

[56] References Cited

U.S. PATENT DOCUMENTS

| 4,841,973 | 6/1989 | Stecker . | |
|---|---|---|---|
| 5,123,413 | 6/1992 | Hasegawa et al. | 607/67 |
| 5,332,401 | 7/1994 | Davey et al. . | |
| 5,387,231 | 2/1995 | Sporer . | |
| 5,501,413 | 3/1996 | Fakhri | 607/75 |
| 5,891,182 | 4/1999 | Flemming | 607/50 |

FOREIGN PATENT DOCUMENTS 8707511  12/1987  WIPO .

*Primary Examiner*—Jeffrey R. Jastrzab
*Attorney, Agent, or Firm*—Ostrolenk, Faber, Gerb & Soffen, LLP

[57] ABSTRACT

The present invention provides a pulsed electric signal having an operating positive amplitude of from 10 to 15 $\mu$A for the use in the provision of a regime of transcranial electrotherapy (TCET) for the prophylaxis and treatment of allergies.

11 Claims, No Drawings

USE OF TCET IN THE PROPHYLAXIS AND TREATMENT OF ALLERGIES

This invention provides a method for the prophylaxis and treatment of allergies.

Transcranial electrotherapy (TCET) is the application of a series of electrical signals of defined amplitude and duration across the head of a patient or test animal by means of percutaneous electrodes generally attached to the external pinnae. TCET is described in U.S. Pat. No. 4,646,744 and in U.S. Pat. No. 5,332,401, the contents of which are incorporated herein by reference thereto.

A preferred method of applying TCET and preferred signal characteristics are described in U.S. Pat. No. 5,332,401, in which means are disclosed to enable the administration to patients of very low current signals which are sub-perception. Such sub-perception treatment has come to be known a Sub-Perception Electrostimulation (SPES).

U.S. Pat. No. 5,332,401 discloses various applications of TCET, including pain amelioration, amelioration of drug withdrawal and amelioration of the effects of stress. However, neither U.S. Pat. No. 5,332,401 nor any other prior publication of the use of TCET either discloses or suggests that TCET might be useful in the prophylaxis and treatment of allergies.

We have now made the surprising discovery that TCET can be used in the prophylaxis and treatment of allergies, especially allergic respiratory conditions.

Thus, according to the present invention there is provided a pulsed electric signal having an operating positive amplitude of from 10 to 15 $\mu$A for use in the provision of a regime of transcranial electrotherapy for the prophylaxis and treatment of allergies.

There is also provided a method for the prophylaxis and treatment of allergies using transcranial electrotherapy wherein a pulsed electric signal having an operating positive amplitude of from 10 to 15 $\mu$A is applied across the head of a human or other animal.

The invention is particularly useful in the treatment of allergic asthma, hayfever, allergic rhinitis, rhinoconjunctivitis and food allergies.

As in the use of TCET for treating pain, drug withdrawal and the effects of stress which is described in U.S. Pat. No. 5,332,401, trains of pulses (i.e. packets of pulses separated by short pauses in relatively short sequences) are used. The signal is preferably an AC signal in which the positive pulse is relatively short and high without being spiked and the following negative pulse is relatively wide and low, the total amount of positive and negative charge being balanced. In a particularly preferred embodiment, the negative pulse has approximately 5–10 times longer duration than the positive pulse.

Patients are typically treated with TCET signals at a frequency of from 9 to 13 Hz, e.g. a frequency of 10 Hz is particularly preferred. Typical trains suitable for use in the present invention contain packets of from 700 to 1000 pulses separated by pauses of from 9 to 11 seconds. e.g. packets of 750 or 1000 pulses (i.e. packets of 75 or 100 seconds in duration), separated by pauses of 10 seconds. The TCET signal may typically be administered in trains of from 28 to 42 complete cycles, e.g. 37 cycles.

Where an AC signal is used, individual signal pulses typically may have a positive duration of about 1.8 to 2.4 msec, e.g. 2.0 msec.

It is essential that the operating positive amplitude of the signal should be 10 to 15 $\mu$A, e.g. about 10–12 $\mu$A. This means that sufficient potential difference should be applied between the two electrodes so that the final positive amplitude of the signal delivered is, for example, 11 $\mu$A, regardless of the impedance of the patient receiving the electrical current. The amplitude of the negative portion of the applied signal is typically <14% of the positive amplitude.

The low-current signals are preferably applied via needle point electrodes similar to those described in U.S. Pat. No. 5,332,401. These point electrodes provide a low impedance when attached to the external pinnae of the patient to be treated.

Studies using pulsed electric signals having an operating positive amplitude of from 10 to 15 $\mu$A in the use of TCET according to the present invention have shown a remarkable effect in the therapy of a wide range of allergies. Remarkably, it appears that treatment with TCET can result not only in short-term amelioration of allergic hyperreactivity but also a long-term prophylaxis which lasts many weeks or even months after the TCET treatment.

The present invention may be further understood by consideration of the following Examples. In each of the following Examples the TCET regime used had the following parameters an AC signal at 10 Hz having an operating positive amplitude of 11 $\mu$A and a positive duration of 2.0 msec, the signal delivered as 37 trains of packets comprising 750 pulses separated by 10 second pauses.

EXAMPLE 1

A 35 year old female spinally injured (paraplegic) subject who had been experiencing chronic 'root' pain for some years participated in a clinical study to determine the efficacy of TCET in the amelioration of pain associated with her spinal injury. TCET treatment was administered twice daily between the times of 09.00–11.00 h and 14.00–1600 h. It was noted that this patient had used a Ventide® inhalant (100 $\mu$g of salbutamol and 50 $\mu$g beclomethasone diproprionate per inhalation), daily throughout the study. This medication had been prescribed to control the allergic asthma that the patient had experienced for many years.

It was discovered that both the saliva and plasma of this subject contained extremely low cortisol levels before and after TCET. Consequently, it was decided to administer TCET to this patient on another occasion when the patient would attempt to abstain from use of her inhalant. On this occasion the patient was able to complete the four day course of TCET treatment for analgesic activity without recourse to Ventide®. Not only did the patient experience more pain relief than on the first occasion but she did not have need for the inhalant during, and two weeks after, TCET treatment. This study was conducted at a time when she would normally be expecting to use the Ventide® inhaler up to 20 or more times per day. It was inferred that TCET treatment had either ameliorated the bronchial allergy or the bronchiospasms the patient experienced.

EXAMPLE 2

A 64 year old female patient was treated using TCET to ameliorate the pain associated with rheumatoid arthritis in the shoulders and other joints, and a neurapraxis in the right hand. This patient previously had also suffered for many years from asthma associated with allergy to various moulds. The patient controlled her bronchial spasms with Ventolin® (salbutamol) inhalant (two or three inhalations of 100 $\mu$g per inhalation, up to five or six times daily) but had been unable to go into the garden in damp weather for many months of the year. The patient received two daily TCET treatments between the times of 09.00–11.00 h and 14.00–16.00 h for four days. During the treatment period the patient did not need to use her inhalant and one week after TCET treatment was able to work in her garden without any reaction to the allergens which would have prevented her from doing so prior to TCET. This patient is now maintained on TCET during the wetter months of the year to control her allergic reaction to moulds and uses no other medication for this. It was concluded that in this patient TCET ameliorated the allergic responses to the moulds.

EXAMPLE 3

A 63 year old male, was treated using TCET for facial pain associated with trigeminal neuralgia. It was noted that the patient experienced recurrent attacks of rhinitis and hay fever as he was sensitive to birth pollen. The allergic condition was previously controlled by Hismanal® (astemizole, 10 mg daily). The patient was required to cease all medication 48 hours prior to commencing TCET. The TCET treatment ameliorated the pain associated with the trigeminal neuralgia sufficiently for the subject to be maintained without further recourse to his analgesic medication. The patient also reported that he had no further use of his antihistamine medication during the next "pollen season". He benefitted sufficiently from the TCET treatment (twice daily for four days) to cease his antihistamine use and had a season free of rhinitis and sneezing.

EXAMPLE 4

As a result of findings such as those shown in Examples 1 to 3 above, it was decided to carry out studies as to the efficacy of TCET in the amelioration of allergic respiratory conditions. Patients selected were non-smokers who presented with known allergic respiratory conditions. All volunteer patients received TCET for seven successive days. TCET was self-administered twice daily between the times of 07.00–09.00 h and 14.00–16.00 h. All patients agreed to cease all other medications 48 hours before commencement of TCET.

4-1. A 52 year old male presented with perennial allergic rhinitis. He also described an allergic response to homemade wine, which had been confirmed as a sensitisation to grape skins. This subject was previously maintained on Zirtek® (cetirizine, 10 mg twice daily) and Syntaris® (flunisolide, 25 µg per dose up to ten times daily) nasal spray. At the time of beginning TCET therapy he reported considerable discomfort, complete nasal obstruction and nasal itching. The TCET treatment was continued for seven days after which time the patient was reportedly symptom free. Estimation of nasal resistance by active anterior rhinomanometry revealed that the airways were completely from. This patient has since remained on TCET therapy with no other support medication or symptoms of rhinitis for nearly two years. It has also been found that the patient's allergy to grape skin has apparently disappeared.

4-2. A 34 year old female patient presented with allergic asthma and rhinoconjunctivitis with confirmed allergy (using skin prick test) to house dust mites (Dermatophagoides species). The patient also reported allergic responses to eggs, milk and shellfish. The patient had been unsuccessfully treated by desensitisation and was being maintained by allergen avoidance and nedocromil sodium (4 mg four times daily). The patient ceased the medication 48 hours prior to beginning TCET therapy, but had access to Ventolin® (salbutamol) inhalant throughout the TCET treatment week to be used only if absolutely necessary. At the end of the treatment week the patient reported using the inhaler only twice (at night) during the first treatment day. Morning PEFR (Peak Expiratory Flow Rate) measured by spirometry had increased 22% and FEV 1 (Forced Expiratory Volume) increased by 35% after the TCET treatment for one week. The patient also reported being able to eat some dairy products without her previous reaction (migraine).

4-3. A 49 year old female presented with allergic rhinoconjunctivitis and asthma associated with allergy to house dust mites (Dermatophagoides species) and cat dander. The patient was receiving Prednesol® (prednisolone, 5 mg twice daily); Bricanyl® (terbutaline sulphate, two inhalations of 250 µg per day) inhalant, Rhinocort Aqua® (budesonide 100 µg per dose) nasal spray and Cusilyn® (sodium cromoglycate 2%) eye drops. The subject was reportedly in considerable discomfort prior to beginning TCET treatment but according to personal diaries was symptom-free after three days of TCET. She remained symptom-free without recourse to any medication to the end of the treatment week. The subject has been maintained on TCET with no pharmaceutical preparations for eighteen months since the initial treatment week. During this time she has remained free of these allergies and has had no recourse to such medication.

4-4. A 34 year old female presented with mild seasonal asthma and rhinitis associated with allergy to grass pollen. This was controlled with Triludan® (Terfenadine, 60 mg twice daily). This patient also had confirmed allergic responses to red wine, yeast paste and crab meat which were controlled by dietary exclusion. All medication ceased 48 hours before commencing TCET therapy although the patient was prescribed Ventolin® (salbutamol) inhalant to be used only if absolutely necessary. The subject did not have recourse to the inhalant during the TCET treatment week and at the end of the treatment week was reportedly symptom free as on the antihistamine medication. The patient remained on TCET reducing the treatments to once daily (between 07.00–09.00 h) and reported no hyperactivity throughout the remainder of the "pollen season".

4-5. A 26 year old laboratory worker had developed severe respiratory allergy to various dander (particularly rodent) through occupational exposure. His condition was controlled by exposure avoidance. The patient reported that he was unable to continue his sporting activity (competitive cycling) without the use of various inhalants because of severe bronchioconstriction induced by exercise. When challenged (5 min vigorous cycling on an exercise machine) he was unable to complete the challenge and when he had recovered sufficiently it was noted his FEV 1 had fallen by 38% from the baseline value estimated before the challenge. Baseline morning FEV 1 volumes were recorded before the patient received TCET for seven days. The morning FEV 1 volume had increased from 2.2–2.5 L and the patient did not experience a bronchiospasm when challenged (5 min vigorous cycling). This patient continued using TCET (once daily between 07.00–09.00 h) with no support medication throughout his winter training period.

4-6. A 53 year old female patient presented with allergic asthma and rhinoconjunctivitis associated with hypersensitivity to both feathers and house dust mite (Dermatophagoides species) allergen. The symptoms were controlled by Prednisol® (prednisolone 5 mg four times daily) and Salbutamin® (salbutamol 100 µg per dose) inhalant. This patient reported sleep apnoea due to bronchial constriction/wheezing at night when she might use her inhalant in excess of three or four times. The patient ceased using her bronchiodilator therapy 48 hours prior to TCET therapy but understood that she could use her inhalant if she experienced nocturnal bronchial constriction. The patient reported that the allergic symptoms had diminished but most importantly by her own diary records she had experienced no disturbance to her sleep on the nights following TCET therapy, had not used her inhalant at all and was not aware of nocturnal coughing or wheezing. She also reported that she no longer felt breathless in the mornings.

It can be concluded from the above examples where TCET was administered to patients exhibiting allergic hyperresponsiveness to various allergens that this treatment was at least as effective, and in some cases more effective in ameliorating the symptoms than the pharmaceutical preparations the patients had been receiving.

TCET appears to be of particular benefit in reducing allergic hyperreactivity associated with rhinitis, conjunctivitis and respiratory allergies including asthma and hayfever and could also be of use in diminishing the response to some food allergens.

I claim:

1. A method of providing a regime of transcranial electrotherapy (TCET) for the prophylaxis or treatment of an allergy, comprising:

applying electrodes to a patient;

applying transcranial electrotherapy to the electrodes, the electrotherapy including an effective dose of a pulsed electric signal having an operating positive amplitude of from 10 to 15 $\mu$A.

2. The method according to claim 1 wherein said signal is an AC signal in which the positive pulse is relatively short and high and the following negative pulse is relatively wide and low, the total amount of positive and negative charge being balanced.

3. The method according to claim 2 wherein the negative pulse has a duration 5 to 10 times longer than that of the positive pulse.

4. The method according to claim 1 wherein the pulsed electric signal has operating positive amplitude of from 10 to 12 $\mu$A.

5. The method according to claim 1 wherein said signal is delivered at a frequency of 9 to 13 Hz in packets of 700 to 1000 pulses separated by pauses of from 9 to 11 seconds.

6. The method according to claim 5 wherein said signal is delivered at a frequency of 10 Hz.

7. The method according to claim 5 wherein said signal is delivered in packets of 750 or 1000 pulses.

8. The method according to claim 5 wherein said packets of pulses are separated by pauses of 10 seconds.

9. The method according to claim 5 wherein said packets are delivered in trains of from 28 to 42 complete cycles.

10. The method according to claim 9 wherein said packets are delivered in trains of 37 complete cycles.

11. The method according to claim 1 wherein the allergy is chosen from the group consisting of allergic asthma, hayfever, allergic rhinitis, rhinoconjunctivitis and food allergies.

* * * * *